United States Patent [19]

Swiderek et al.

[11] Patent Number: 5,741,701
[45] Date of Patent: Apr. 21, 1998

[54] CELL CULTURE SUBSTRATES AND METHODS OF USE

[75] Inventors: Mark S. Swiderek, Gloucester; Frank J. Mannuzza, Burlington, both of Mass.

[73] Assignee: Becton, Dickinson and Company, Franklin Lakes, N.J.

[21] Appl. No.: 377,887

[22] Filed: Jan. 25, 1995

Related U.S. Application Data

[62] Division of Ser. No. 233,028, Apr. 25, 1994, abandoned.

[51] Int. Cl.$^6$ .................................................. C12M 3/06
[52] U.S. Cl. .......................... 435/297.1; 435/240.241; 435/240.243; 435/297.5; 435/810
[58] Field of Search ........................ 435/1, 29, 30, 435/240.241, 240.243, 284, 285, 299–301, 311, 810, 297.1, 297.5, 1.1; 530/356

[56] References Cited

U.S. PATENT DOCUMENTS

| | | | |
|---|---|---|---|
| 2,934,446 | 4/1960 | Highberger et al. | 530/356 |
| 4,233,360 | 11/1980 | Luck et al. | 428/310 |
| 4,600,533 | 7/1986 | Chu | 530/356 |
| 4,904,596 | 2/1990 | Hakomori | 435/240.27 |
| 4,996,154 | 2/1991 | Gabriels | 435/240.241 |
| 5,256,418 | 10/1993 | Kemp et al. | 424/423 |
| 5,354,666 | 10/1994 | Danielson et al. | 435/70.3 |

OTHER PUBLICATIONS

Gelman et al. "Collagen Fibril Formation." The Journal of Biological Chemistry. vol. 254, No. 1 (1979) pp. 180–186.
Krief et al. "Transcriptional Modulation by n–Butylric Acid . . . " The Journal of Biological Chem. vol. 269, No. 9 (1994) pp. 6664–6670.
Williams et al. "Collagen Fibril Formation." The Journal of Biological Chem. vol. 253, No. 18 (1978) pp. 6578–6585.

*Primary Examiner*—William H. Beisner
*Attorney, Agent, or Firm*—Donna R. Fugit

[57] ABSTRACT

Cell culture substrates comprising dried films of native fibrillar collagen produced by a method in which collagen fibers are hydrolyzed in acid, solubilized, and reformed as gels on porous surfaces under non-physiologic salt conditions to produce large fibers with the striations characteristic of collagen fibers found in vivo. The gels are collapsed onto the porous surfaces by drawing the interfibril fluid out of the gel through the underside of the porous surface and then dried to form films. Dried collagen films made in this manner retain native fibrillar collagen structure and excellent diffusion characteristics. Native fibrillar collagen films produced according to the methods of the invention are useful as cell culture substrates. They have particularly advantageous properties for growth and differentiation of epithelial cells. This effect is synergistically enhanced by addition of butyric acid as a differentiation inducing agent.

5 Claims, 7 Drawing Sheets

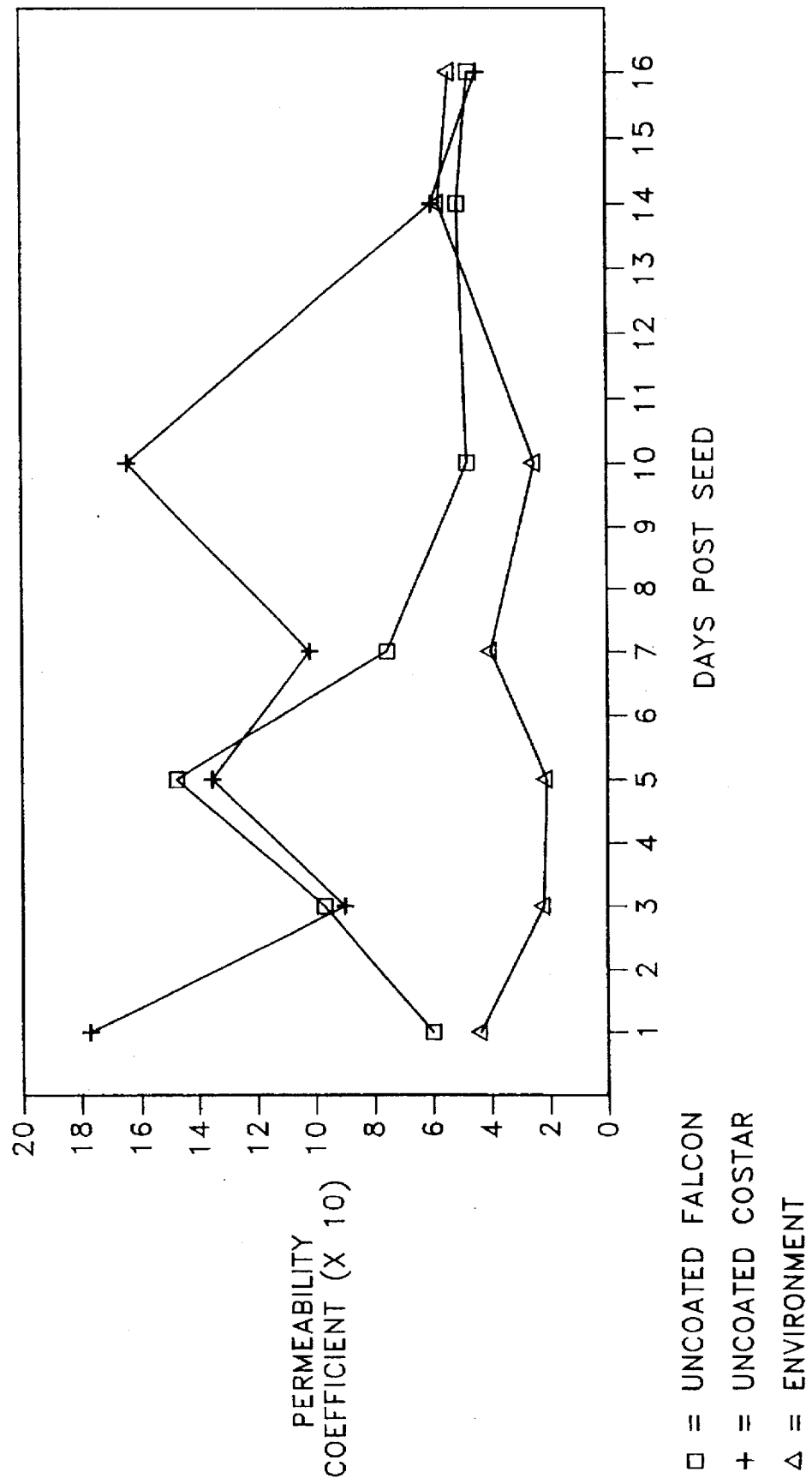

CELL CULTURE SUBSTRATES AND METHODS OF USE

This is a division of application Ser. No. 08/233,028, filed Apr. 25, 1994, abandoned.

FIELD OF THE INVENTION

The present invention relates to in vitro cell culture. In particular, the invention relates to collagen substrates for in vitro cell culture and methods for promoting differentiation of cultured epithelial cells.

BACKGROUND OF THE INVENTION

In vivo, several types of differentiated epithelial cells exhibit polarized morphology consistent with their function. For example, intestinal enterocytes (the absorptive cells of the intestine) are responsible for the uptake of material from the intestine and are morphologically polarized when fully differentiated. That is, the apical (lumenal) surface facing the interior of the gut comprises numerous microvilli which increase the surface area for transport. On the basal (ablumenal) surface which faces away from the interior of the gut the cells are in contact with the extracellular matrix. The extracellular matrix plays a complex role in a diverse group of cellular functions, including biogenesis of cellular polarity, cell migration and cell differentiation. Differentiated intestinal epithelial cells have therefore been used extensively in culture as a model system for studying intestinal transport (e.g., of drugs and metabolic products), mechanisms of infection (e.g., interactions between infectious agents and cells) and enzyme induction and regulation. The majority of studies being done on transport, infection and metabolism utilize established intestinal epithelial cell lines such as Caco-2 (W. Rubas, et al. 1993. *Pharmaceutical Research* 10, 113–118; G. Ranaldi, et al. 1992. *Antimicrobial Agents and Chemotherapy*, 36, 1374–1381; W. Bement, et al. 1993. *J. Cell Biology* 121, 565–578; M. Bernet, et al. 1993. *Applied and Environmental Microbiology* 59, 4121–4128), IEC-18 (T. Ma, et al. 1992. *J. Lab. Clin. Med* 120, 329–341), IEC-6, T84 (B. McCormick, et at. 1993. *J. Cell Biol.* 123, 895–907) and RIE-1. In contrast, studies on the process and nature of epithelial cell differentiation generally use primary cell cultures. The epithelial cells lining the airways and the kidney tubules are also morphologically polarized, and when differentiated exhibit characteristic phenotypes and functions (e.g., transport, enzyme induction and membrane interactions).

The cells of established epithelial cell lines and primary epithelial cell cultures are generally initially undifferentiated. Therefore, in order to study the functions of differentiated epithelial cells or the mechanisms by which the cells become differentiated, they must first be induced in culture to differentiate. The established cell lines exemplified above undergo spontaneous differentiation in culture some period of time after the cells have reached confluence. At the present time, the conventional method for producing cultures of differentiated enterocytes is simply to culture the undifferentiated cells under normal cell-growth conditions until they spontaneously differentiate, either on cell culture substrates such as collagen or on solid surfaces without any substrate (e.g., on the surface of a tissue culture dish or on a porous membrane).

The degree of differentiation of intestinal epithelial cells in culture can be determined by measuring the electrical resistance across the cell monolayer (Trans Epithelial Electrical Resistance—TEER). Increased resistance correlates with a higher degree of differentiation in the enterocyte. Resistance is measured in ohms and is inversely proportional to the area being measured, therefore: TEER=ohms× area measured=ohms*cm². Caco-2 cell cultures must be maintained for approximately 14–30 days post confluence in order to differentiate fully and develop the TEER of mature cells. IEC-18 cells require approximately 4 days in culture before they differentiate fully and develop the TEER of mature intestinal epithelial cells. The permeability coefficient is another means for measuring the degree of differentiation of intestinal epithelial cells in culture. The permeability coefficient is a measure of how readily a material (e.g., mannitol, rifampin or d-cycloserine) will pass through the cell monolayer. A larger permeability coefficient indicates that more material passes through the cell monolayer and a low permeability coefficient indicates that less material is able to pass through. Fully differentiated enterocytes with fully developed barrier function exhibit different permeability coefficients for different materials. In general, Caco-2 cells also require about 14–30 days in culture before they exhibit the permeability characteristics of fully differentiated intestinal epithelial cells. IEC-18 cells require about 5 days in culture to reach full differentiation as evidenced by permeability characteristics. Such long term culturing is time consuming and laborious. It requires planning research studies as much as 2–4 weeks in advance so that differentiated cells will be available at the time they are needed for transport, infection and metabolic studies.

Epithelial cells and many other cell types are often cultured on collagen substrates to improve cell attachment and provide an environment more similar to that found in vivo. In conventional methods to form the substrates, extracted, solubilized collagen is simply dried on or adsorbed onto a surface, forming an amorphous collagen layer or film. Alternatively, soluble collagen in acid solution may be polymerized on a surface by exposure to ammonium hydroxide vapors or by neutralization. In other methods, collagen is precipitated by salting out of solution. The collagen may be chemically cross-linked for structural stability by exposure to ultraviolet light or chemical agents such as formaldehyde or glutaraldehyde. The structure and properties of the collagen substrate varies depending on the process by which it is made. In general, the native fibrillar structure of collagen which is found in vivo is not reproduced, and diffusion of materials through the collagen substrate is often significantly reduced as compared to native collagen. The collagen cell culture substrates currently available are generally produced under non-physiologic conditions and comprise either a layer of amorphous collagen having little organized fibrillar structure or a membrane composed of chemically cross-linked collagen fibers. Amorphous collagen substrates are produced by drying an acid solution of soluble collagen on a surface. Collagen films are generally produced by treatment of soluble collagen with alkali (usually ammonia vapor) to induce polymerization on the desired surface. Chemical cross-links introduced by cross-linking agents such as glutaraldehyde are often employed to stabilize polymerized or amorphous collagen on surfaces and, in addition, to provide sites for attachment of proteins such as growth factors. Both of these non-native collagen structures have satisfactory structural stability but poor diffusion characteristics which reduce the availability of nutrients and other materials to cultured cells. Amorphous collagen films have particularly poor diffusion characteristics due to the lack of fibril organization. In addition, in many cases the collagen used to form the substrate is devoid of the non-helical ends of the collagen fibers (the teleopeptides), which have been removed during the extraction process by digestion with pepsin. These preparations also result in non-native collagen structures when polymerized, and although some fibrillar structures are formed they are poorly organized due to the absence of teleopeptides.

Amorphous, chemically cross-linked and alkali denatured collagen films for use as cell culture substrates are often dried to improve shelf life and to eliminate the need to prepare the cell culture substrate prior to each use. Native fibrillar collagen cell culture substrates reported in the prior art, however, are prepared and used only in the form of firm, adherent gels of native fibrils. These are most often produced by warming a cold, neutralized solution of soluble collagen to induce polymerization and precipitation of native fibrils. They are not dried for storage, as previous attempts to collapse and dry the gels have resulted in loss of the native structure, suboptimal fiber formation and poor permeability characteristics. Native fibrillar collagen cell culture substrates must therefore be made just prior to use, increasing the labor and inconvenience associated with studies involving cell culture on native fibrillar collagen.

Kemp, et al. (U.S. Pat. No. 5,256,418) disclose methods of making collagen constructs such as tissue equivalents. The method first requires formation of a collagen concentrate by means of development of an osmotic gradient across a semipermeable membrane. The semipermeable membrane allows only the passage of solute, and is not permeable to collagen. The collagen is then polymerized onto the semipermeable membrane to form the collagen construct and, typically, cross-linked. In contrast, the methods of the invention concentrate after polymerization rather than prior to polymerization. That is the fibrils and fibers polymerize from the collagen solution directly onto the porous surface. Concentration follows polymerization and is not accomplished by osmosis, but rather by drawing fluid out of the polymerized collagen gel through a macroporous material which would be permeable to unpolymerized collagen. These inventive process steps are essential to forming dried collagen films which retain the fibrillar structure of native collagen.

The present invention for the first time provides methods for making dried collagen films for cell culture in which the collagen is in native fibrillar form. These cell culture substrates are formed using native soluble collagen monomers and conditions which maintain the native configuration during polymerization, i.e., without pepsin digestion, chemical cross-linking or denaturation. Also provided are the native fibrillar collagen substrates for cell culture and methods for using them in cell culture, particularly culture of morphologically polarized epithelial cells. It has been discovered that the native fibrillar collagen cell culture substrates of the invention promote the development of diffferentiated functions in cultured epithelial cells, and therefore significantly reduce the time required to obtain differentiated cultures for studies which require the functions of mature polarized epithelial cells.

As used herein, the following terms are defined as follows:

Native fibrillar collagen refers to collagen exhibiting organized fibrillar structure similar to that found in vivo, with large fibers composed of multiple fibrils as well as the striations and banding patterns characteristic of native collagen. This is in contrast to the collagen films and membranes of the prior art, in which fibrils (if present) are poorly organized with few fibers and striations.

Differentiation of intestinal epithelial cells refers to development of barrier functions characteristic of mature enterocytes, as evidenced by electrical resistance across a monlayer of intestinal epithelial cells and permeability coefficients.

Cell culture substrate refers to the native fibrillar collagen films of the invention when they are used as substrates for attachment and growth of cells in vitro.

SUMMARY OF THE INVENTION

Cell culture substrates comprising dried films of native fibrillar collagen have been produced from monomeric collagen derived from collagen fibers solubilized in acid and filtered to remove aggregates. Native collagen fibrils and fibers are then reformed as gels on porous surfaces under conditions which produce large, organized fibers with the striations characteristic of native collagen fibers found in vivo. The gels are collapsed onto the porous surfaces by drawing the interfibril fluid out of the gel through the underside of the porous surface and then dried to form films. Dried collagen films made in this manner retain native fibrillar collagen structure and excellent diffusion characteristics. Native fibrillar collagen films produced according to the methods of the invention are useful as cell culture substrates and have particularly advantageous properties for growth and differentiation of morphologically polarized epithelial cells. They significantly reduce the time required to achieve expression of differentiated functions in epithelial cells in culture as compared to the collagen cell culture substrates of the prior art. In addition, this effect is synergistically enhanced by addition of butyric acid to the cell culture.

DESCRIPTION OF THE DRAWINGS

FIG. 7 is a graph showing the development of mannitol permeability coefficients in cells cultured on uncoated polyethyleneterephthalate membranes (Uncoated Falcon), uncoated polycarbonate membranes (Uncoated Costar) and on native fibrillar collagen with butyric acid induction according to the invention (Environment).

DETAILED DESCRIPTION OF THE INVENTION

Figure 1A:
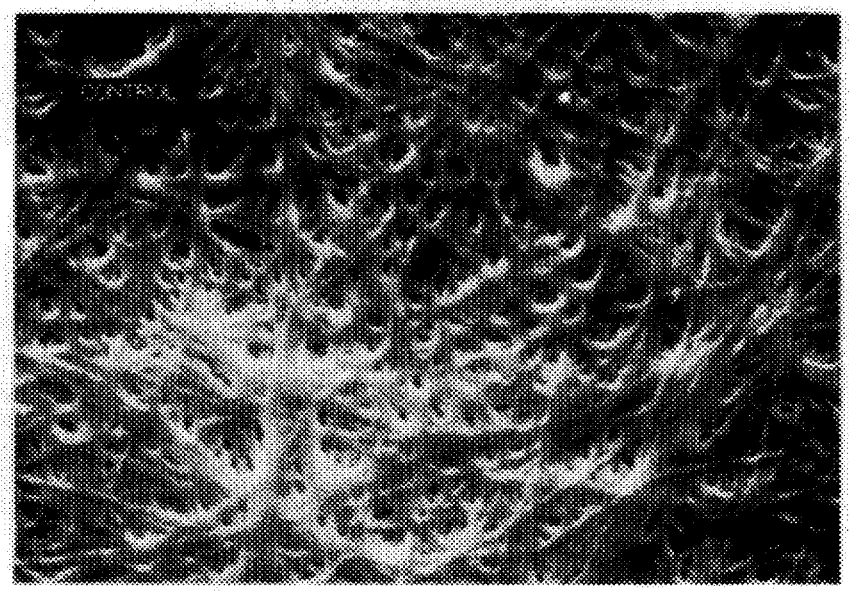
FIG. 1A is an electron micrograph showing the structure of the native fibrillar collagen of the invention (Control), as compared to FIG. 1B which shows the amorphous collagen structure produced by methods of the prior art (AMO).

The native fibrillar collagen cell culture substrates of the invention are produced as dried films on porous surfaces. They retain the native fibrillar collagen structure in dried form and therefore have the improved permeability characteristics of cast collagen gels and the storage stability of amorphous or cross-linked collagen films. The dried membrane may be removed from the porous surface for cell culture if desired, but it is generally preferable to use the native fibrillar collagen cell culture substrate on its porous surface for added structural support and ease of handling. Cells on the upper surface of the cell culture substrate may be exposed to media, growth factors, and other materials by diffusion thereof through the underside of the porous surface and the cell culture substrate, as the cell culture films of the invention exhibit excellent diffusion properties.

Type I, Type II, Type III and Type V collagens are very similar structurally. All of these and any other collagen which has a similar structure may be used to produce the native fibrillar collagen films of the invention. Collagen may be prepared from any suitable source (e.g., rat tail, bovine achilles tendon, pig tendon, etc.) using any of the conventional methods for preparation of solubilized collagen. See, for example, R. Grinnell, et al. 1981. *J. Cell Sci.* 48, 19–34; B. R. Williams, et at. 1978. *J. Biol. Chem.* 253, 6578–6585; R. A. Gelman, et al. 1979. *J. Biol. Chem.* 254, 11741–11745; P. L. Iversen, et al. 1981. *In Vitro* 17, 540–552; H. K. Kleinman, et al. 1979. *Anal. Biochem.* 94, 308–312. In a preferred method, a collagen source is extracted in 0.5M acetic acid. This solution is dialyzed against a lower concentration of acid, preferably 0.1% (about 0.02M) acetic acid, so that the collagen fibers are completely solubilized. The solubilized collagen solution is then sterile filtered to remove any remaining aggregates, e.g., using a 0.2 µm filter.

Salt concentrations which are about physiologic or higher, preferably about 0.15M to about 1M, are used to promote formation of large native collagen fibers. At salt concentrations below physiologic there is little, if any, collagen fiber formation. However, as salt is increased to approximately physiologic concentrations fiber formation becomes essentially complete, with little amorphous collagen being present. As salt is increased above physiologic concentrations, larger and larger fibers are formed. However, when the salt concentration reaches about 1.1M, fiber formation is again essentially completely absent. When the solubilized collagen is in acidic solution, the pH may be raised to approximately 6–8, preferably about 7.0–7.4, concurrently with adjustment of the salt concentration by addition of cold NaOH in a buffer such as phosphate buffered saline (PBS) to give a final salt concentration of about 0.15M-1M, preferably at least about 0.6M (about 4× physiologic salt). The collagen is maintained in solution by storage in the cold (usually about 4° C.) until polymerization of collagen fibrils and fibers is desired. The collagen concentration is not critical for formation of the native collagen fibers, but is preferably about 25–500 µg/cm² of porous surface when intended for use as a cell culture substrate, more preferably about 50–200 µg/cm².

The native fibrillar collagen films of the invention are prepared from the solutions of solubilized collagen as follows. The cold collagen solution is pipetted onto the desired surface. When the native fibrillar collagen films are to be used as cell culture substrates, porous surfaces are preferred. Suitable porous surfaces for formation of native fibrillar collagen substrates include natural or synthetic polymers such as cellulose membranes, porous polycarbonate, porous polytetrafluoroethylene (e.g., TEFLON mesh membranes such as Millipore CM), nylon membranes and meshes, glass filters, porous polyethyleneterephthalate, and various types of filters (e.g., ANOPORE aluminum crystal filters). The porous surface should have a pore size which is small enough to prevent the collagen solution from flowing through prior to polymerization but large enough to allow passage of fluids such as media and the interfibril fluid. In general, membranes having pore sizes of about 0.2–8 µm provide the desired properties. A surface comprising a membrane with pores approximately 1 µm in size is preferred for most general cell culture applications such as material transport studies. Pore sizes of about 3 µm–8 µm are preferred for cell migration studies such as tumor cell migration and leukocyte trafficking.

While native fibrillar collagen will form on any membrane material using the methods of the invention, there may be positive or negative effects of the selected membrane in certain biological applications. Some of these effects are discussed in more detail below as they relate to development of permeability coefficients in cultured cells. While etched membranes are preferred for transport studies, cast membranes may also be used if the permeability coefficient of the material being tested does not exceed the permeability coefficient of the membrane (i.e., the permeability coefficient of the membrane is not a limiting factor). For convenience in cell culture applications, culture plate inserts which incorporate porous membranes are preferred (e.g., BIOCOAT Control Cell Culture Insert, Collaborative Biomedical Products; TRANSWELL, Costar; MILLICELL Culture Plate Insert, Millipore Corporation). PET membranes are preferred over materials such as high density polycarbonate for applications involving microscopy due to their higher transparency. For these reasons, different membranes may therefore be preferred for different applications and can be routinely selected by one skilled in the art.

Upon application to the porous surface, the temperature of the cold, neutralized collagen solution is allowed to increase to about 15°–35° C. to initiate native collagen fibril and fiber formation. Temperatures at approximately room temperature are preferred. As the temperature of the collagen solution increases, native fibrils begin to polymerize and gel on the porous surface, coating the upper side thereof. The gel comprises large, organized fibers of collagen with the striations characteristic of native collagen as well as entrapped fluid from the collagen solution (interfibril fluid). In general, about 0.5–3 hours at room temperature is sufficient to obtain complete polymerization on a porous surface such as the membrane of a cell culture insert. The interfibril fluid of the polymerized collagen is then drawn out of the gel through the underside of the porous surface. This process collapses the gel onto the porous surface and forms a thin membrane of native collagen fibers and fibrils. The fluid may be removed by any suitable means, such as placing the underside of the porous surface on an absorbant material for 3 min. to overnight or applying a gentle vacuum to the underside of the porous surface. It is important for optimum native fiber formation to thoroughly remove interfibril fluid from the polymerized collagen gel through the underside of the porous surface prior to drying the film. While not wishing to be bound by any particular means by which the invention works. Applicants believe that drawing interfibril fluid through the underside of the porous surface allows removal of salts and other materials which would otherwise remain in the final collagen film and crystallize during drying, thus disrupting formation of an uninterrupted, continuous membrane of fibers. Disruption of the collagen film results in disruption of the continuity of the cell monolayer cultured on it. The improved structure of the collagen film is an important advance provided by the invention, as loss of as little as 5% of cell monolayer integrity may result in as much as a 95% loss in barrier properties. For this reason, barrier function model systems are difficult to set up reproducibly using prior art methods.

Figure 1B:
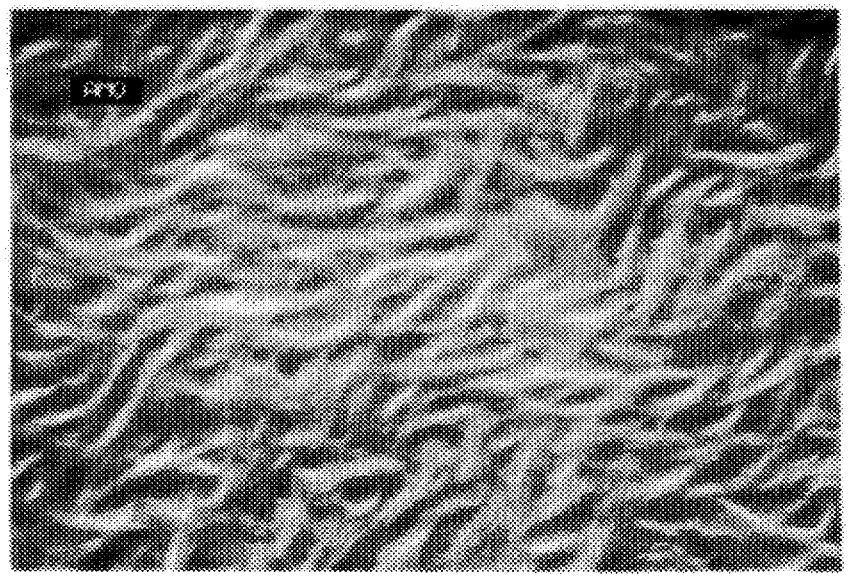

The collagen gels are then dried on the porous surfaces to form films of native fibrillar collagen. They may be air dried, oven dried or dried under vaccuum at a temperature between room temperature and about 40° C. for about 0.5 hr. to overnight. Preferably, drying is at room temperature for approximately 16–20 hr. After drying, the films may be sterilized, for example by irradiation (e.g., ultraviolet light, electron beam or gamma irradiation) or exposure to ethylene oxide gas. The native fibrillar collagen films of the invention, in contrast to the collagen cell culture substrates of the prior art, retain their native fibrillar structure when dried and therefore more closely resemble an in vivo collagen substrate. The electron micrographs of FIG. 1 demonstrate the difference in structure between the native fibrillar collagen films of the invention (Control) and the amorphous collagen films of the prior art which show no formation of native collagen fibers (AMO). One embodiment of the invention is therefore a dried native fibrillar collagen film, including such films for use as cell culture substrates.

Organizational entropy drives the polymerization reaction of the invention. As the physical mechanism is the same for other proteins which undergo a similar type of self-assembly, any protein or proteins which spontaneously form organized polymeric structures in vitro will produce native constructs when substituted for collagen in the foregoing production process. These include proteins which form homopolymers (e.g., fibronectin or laminin) and heteropolymers (e.g., laminin with collagen IV or laminin with proteoglycans). Mixtures of extracellular matrix components which comprise proteins which undergo self assembly, such as MATRIGEL (Collaborative Biomedical Products, Inc.), may also be polymerized and dried according to the methods of the invention to produce native constructs. MATRIGEL forms a sticky, loose gel which blots well to form a glassy membrane. Although all such proteins may not produce gels which collapse and form a film in the same manner as collagen gels when the interfibril fluid is removed, withdrawal of the interfibril fluid from the polymerized substrate and drying should still allow retention of the native construct in the final product.

A wide variety of materials, including bioactive proteins, may be co-polymerized with the collagen or incorporated into the film by adsorption to the collagen, as desired for a particular cell culture system. These include, but are not limited to, cells, antibodies, enzymes, receptors, growth factors, additional components of the extracellular matrix, cytokines, hormones and drugs. These materials may be added to the cold collagen solution at the appropriate concentration for the selected cell culture application. Polymerization of the native collagen fibrils as described above binds the material to or copolymerizes the material with the collagen fibers. Due to the open fiber structure of the cell culture substrate, biologically active added materials are readily available to the cultured cells to moderate or regulate their properties or behavior.

As a result of the method used to remove the interfibril solution, less than 10% remains entrapped in the collagen membrane prior to drying. A variety of polymerization conditions, including nonphysiological conditions, may therefore be used to produce the cell culture films without concern for negative effects of non-collagenous residuals such as salts or organic materials on the cell environment. Collapsing the gel onto the porous surface and drying to form the fibrillar collagen film provides a uniform surface for even distribution of cells and, if desired, a high concentration of collagen (about 5–10 mg/ml). The native fibrillar collagen structure provides the in vivo spatial orientation for binding of cell receptors not found in amorphous collagen cell culture substrates. The fibrillar collagen network also provides a textured surface which results in a higher collagen surface area on each film than is found on the essentially two-dimensional surfaces of other collagen cell culture substrates. The native fibrillar collagen cell culture substrates bind cells more avidly and uniformly to their surfaces than do the collagen substrates of the prior art. That is, many diverse cell types applied to the surface bind to it rapidly and completely (e.g., epithelial cells, endothelial cells and fibroblasts). As described below, the native fibrillar collagen cell culture substrates of the invention also promote more rapid development of differentiated functions in epithelial cells in culture. One example of this property is the development of barrier function in cultured intestinal epithelial cells, as measured by development of mannitol permeability coefficient and electrical resistance.

Dried native fibrillar collagen cell culture films may be substituted for conventional collagen cell culture substrates in any of the cell culture protocols and methods known in the art. In a preferred embodiment, the native fibrillar collagen cell culture substrate on the porous surface is placed in the well of a tissue culture plate with the underside of the porous surface in contact with an appropriate culture medium. This allows the culture medium to flow through the porous surface into contact with the cell culture substrate. The culture medium and other materials which may be present in it diffuse through the cell culture substrate into contact with cells seeded on its surface. For ease of handling, the cell culture substrate may be prepared on the microporous membrane of a cell culture insert. The cells to be cultured may be seeded at subconfluence or confluence on the upper surface of the substrate and placed under environmental conditions appropriate for cell growth. For example, when the cell culture substrate is prepared on the surface of the membrane of an insert for the well of a culture dish, a small amount of growth medium is placed in the well. The insert is placed in the well so that the culture medium contacts the underside of the porous membrane and diffuses through the cell culture substrate into contact with cells seeded on the substrate surface. As described below, the native fibrillar collagen cell culture substrates of the invention have been found to have particularly advantageous properties for inducing development of diffferentiated functions in cultured epithelial cells.

For example, the native fibrillar collagen films of the invention have particularly advantageous properties when used as substrates for culturing intestinal epithelial cells to obtain differentiated enterocytes. The inventive cell culture substrates enhance expression of barrier function in these cells as compared to the collagen cell culture substrates of the prior art. One embodiment of the invention is therefore a method for producing differentiated intestinal epithelial cells in culture using the inventive native fibrillar collagen cell culture substrates. Further, intestinal epithelial cells in culture express barrier functions more rapidly on the native fibrillar collagen cell culture substrates than on conventional collagen substrates even in the absence of differentiation inducing agents. However, an inducing agent may be employed to reduce the time required for differentiation even further. Butyric acid is one material which has been used to modify the growth and differentiation properties of cells in culture (A. Souleimani, et al. 1993. *FEBS Lett.* 326, 45–50). It has now been found that butyric acid acts synergistically with the native fibrillar collagen cell culture substrates to further enhance the rate of differentiation over culturing on the substrate alone. Cells which on conventional collagen cell culture substrates or on surfaces without substrates require a minimum of about 2 weeks to develop mature barrier function (e.g., Caco-2) differentiate in under four days when cultured on the cell culture substrates of the invention with butyric acid induction. Cells which require at least four days post seeding under conventional conditions to fully differentiate (e.g., IEC-18) do so within about 48 hours using the inventive cell culture substrates with butyric acid induction. The butyric acid inducing agent may be added to the cells by addition to the culture medium at a concentration of about 4–20 mM, preferably about 5 mM butyric acid.

Any cell culture medium appropriate for growth and differentiation of epithelial cells may be used in cell cultures employing the present collagen cell culture substrates. These include, but are not limited to, DMEM, MEM, M-199 and RPMI. Supplements, as are known in the art, may be added to the culture medium and include serum (e.g., FBS or calf serum), serum-containing supplements (NU-SERUM), and serum-free supplements (MITO+). A preferred cell culture medium for intestinal epithelial cells is DMEM supplemented with MITO+ Serum Extender (Collaborative Biomedical Products, Bedford, Mass.) to provide a fully defined, serum-free cell culture environment.

The components for use in the above method for promoting expression of differentiated functions in cultured epithelial cells, preferably for promoting expression of barrier function in cultured intestinal epithelial cells, may be conveniently packaged in the form of a kit. The kit may include, for example, 1) a cell culture medium such as DMEM, 2) serum or a serum-free media supplement, 3) native fibrillar collagen cell culture substrates on porous surfaces for use in the wells of a tissue culture dish (e.g., on culture dish well inserts), and 4) optionally, a differentiation medium comprising a differentiation inducing agent such as butyric acid. The kit may also optionally include a tissue culture dish or other cell culture accessories and reagents which may be required to carry out the epithelial cell culture and differentiation method.

The following examples are given to illustrate certain embodiments of the invention and are not to be construed as limiting the invention as defined by the appended claims and equivalents thereof.

EXAMPLE 1
PREPARATION OF NATIVE FIBRILLAR COLLAGEN CELL CULTURE SUBSTRATES

The following experimental example describes the preparation of native fibrillar collagen cell culture substrates on 1 µm polyethyleneterephthalate (PET) membranes in PET cell culture inserts. In this example, about 200 µg of collagen were added per cm$^2$ of the membrane.

Soluble collagen in acid solution was prepared from rat tail tendon as described by Bornstein (1958. *Lab. Invest.* 7, 134–137), with dialysis against dilute acid and sterile filtration to remove aggregates. The cold acid solution of rat tail collagen was adjusted to 674 µg/ml by addition of 10×DPBS/NaOH to obtain a final concentration of 4×DPBS, pH 7.4, and the mixture was kept on ice until use. Insert holders were placed in tissue culture dishes. The cell culture inserts were placed in the insert holders with sterile forceps and lids were placed on the dishes until use. The collagen coating solution (0.10 ml) was dispensed onto each membrane, the culture dish lid was replaced and the dish was rocked gently to evenly distribute the coating solution on the membrane. The coated membranes were then equilibrated to room temperature to allow the collagen to polymerize (1.5–2.0 hrs.), keeping the membranes in a humid environment to prevent premature drying.

When the collagen had polymerized, the insert holder was placed on a sheet of blotting paper so that all of the membranes were in contact with the blotting paper. A polypropylene sheet was placed on top of the insert holder and downward pressure was applied for about 10–15 sec. For convenience when multiple insert holders were being handled, the insert holders were stacked by placing a sheet of blotting paper on the polypropylene sheet and a second insert holder on top of the blotting paper covered with a second polypropylene sheet, etc. until the stack of insert holders was four to five high. The last element on top of the stack was a polypropylene sheet. After the last insert holder was in place, the stack was weighted down and 30 min. was allowed for completion of blotting. When all substrates were completely blotted the insert holders were replaced in the tissue culture dishes and covered.

The tissue culture dishes with the blotted cell culture substrates were transferred to a laminar flow hood and air dried overnight. Alternatively, the substrates were oven dried. The native collagen cell culture substrates were then sterilized in the tissue culture dishes by exposure to 0.05–0.06 Joules of ultraviolet light and stored at 4° C. in sealed bags until use.

EXAMPLE 2
ELECTRICAL RESISTANCE ASSAY

Native fibrillar collagen cell culture substrates on 1 µm PET membranes in cell culture inserts were prepared as in Example 1 and used to culture Caco-2 cells for measurement of the development of electrical resistance (TEER), an indication of cell differentiation.

The culture medium was aspirated from one 80–100% confluent T-75 flask of Caco-2 cells. The flask was rinsed with 12 ml of DPBS, which was also aspirated. The cells were incubated at 37° C. with trypsin (10 ml) until all were detached from the surface of the flask. Approximately 10 ml of DMEM with 10% FCS was added to neutralize the trypsin. Cells were pelleted by centrifuging at 1500 rpm and resuspended in DMEM with MITO+ Serum Extender at 400,000 cells/ml.

Culture medium (1 ml/well) was added to the wells of a tissue culture dish, each well containing a cell culture substrate. Approximately 0.5 ml of cell suspension (2×10$^5$ cells) was pipetted onto the surface of each cell culture substrate and the cultures were incubated at 37° C. in 5–10% $CO_2$, 100% humidity for 24 hrs. After 24 hrs. the medium was aspirated from each well and replaced with 1 ml of DMEM with 5 mM butyric acid in the well and 0.5 ml of the same medium on top of the cell culture substrate. The cultures were incubated at 37° C., 5–10% $CO_2$, 100% humidity. Each day following induction by addition of butyric acid, the electrical resistance of the cell monolayers was measured using an ENDOHM tissue resistance measurement chamber (World Precision Instruments, Inc., Sarasota, Fla.).

TEER≧150 ohmcm² is indicative of complete differentiation of Caco-2 cells in culture. Caco-2 cells cultured on the native fibrillar collagen cell culture substrates with induction by butyric acid achieved TEER≧150 ohmcm² by the third day in culture (two days after addition of butyric acid). In contrast, differentiation of Caco-2 cells cultured on conventional collagen substrates or surfaces without substrate requires 14-30 days of culture as reported in the literature. Butyric acid has not previously been used to induce differentiation in cultured Caco-2 cells. Promotion of differentiation in this experiment, however, is not due solely to the presence of butyric acid, as expression of barrier function in Caco-2 cells is also significantly promoted when they are cultured on native fibrillar collagen cell culture substrates in the absence of this inducer (see Example 4). It is therefore believed that the the inventive native fibrillar collagen cell culture substrate itself has differentiation-promoting properties which are absent from prior art collagen substrates. These properties interact synergistically with butyric acid to further promote cell differentiation and further decrease the culture time required to achieve differentiated intestinal epithelial cell cultures.

The foregoing experiment was repeated using IEC-18 cells. For these cells, TEER=28 ohmcm² was used as the indicator of complete differentiation. When cultured on the native fibrillar collagen cell culture substrates of the invention, with butyric acid induction, IEC-18 cells achieved this level of electrical resistance by the second day in culture (one day after addition of butyric acid). Literature reports for IEC-18 cells cultured on conventional collagen substrates or on surfaces without substrates disclose that four days of culture are required to achieve TEER=28 ohmcm². As discussed above, the enhanced rate of differentiation observed is partially the result of the unique properties of the native fibrillar collagen cell culture substrate itself, but in addition a synergistic effect between the substrate and induction with butyric acid has been observed.

EXAMPLE 3
PERMEABILITY COEFFICIENTS

Caco-2 cell monolayers on native fibrillar collagen cell culture substrates were prepared as described in Example 2. Following the addition of media containing 5 mM butyric acid, cell culture inserts with the cell culture substrates were removed daily from the tissue culture well and placed in a well containing 1 ml of PBS to monitor the development of barrier function. The material to be tested for permeability (300 µl ³H-mannitol, rifampin or d-cycloserine) was added to the lumenal (upper) side of the cell culture substrate and the substrate was incubated at room temperature for about 10 min. to 3 hr. The cell culture insert was then removed with forceps to a well containing fresh PBS and the concentration of the test material in the PBS on the ablumenal (well) side of the substrate was measured by scintillation counting or spectrophotometry.

Caco-2 cells required three days in culture (two days after addition of butyric acid) to achieve permeability coefficients indicating full differentiation. These permeability coefficients were ≦4×10⁻⁶ cmsec for mannitol, 13.1×10⁻⁶ cmsec for rifampin and 34.0×10⁻⁶ cmsec for d-cycloserine. In contrast, the literature for Caco-2 cells reports that 14-30 days in culture are required on conventional collagen substrates or on surfaces without substrate to achieve similar permeability coefficients: ≦4×10⁻⁶ cmsec for mannitol, 13.4×10⁻⁶ cmsec for rifampin and 38.2×10⁻⁶ cmsec for d-cycloserine (Rubas, et al., supra and Ranaldi, et. al., supra).

IEC-18 cells were tested in a similar experiment These cells achieved a mannitol permeability coefficient of ≦7×10⁻⁶ cmsec after two days in culture (one day after addition of butyric acid). The literature reports that five days in culture on conventional collagen substrates or on surfaces without substrate are required to achieve this degree of differentiation in IEC-18 cells (Ma, et al., supra).

EXAMPLE 4
DIFFERENTIATION OF INTESTINAL EPITHELIAL CELLS ON COLLAGEN CELL CULTURE SUBSTRATES

The native fibrillar collagen cell culture substrates of the invention were compared to commercially available collagen cell culture substrates and to uncoated membranes customarily used for cell culture: 1) BIOCOAT Collagen I Cell Culture Inserts (Collaborative Biomedical Products, Bedford, Mass.—amorphous rat tail collagen on 1 µm PET membranes), 2) TRANSWELL cell culture inserts (0.45 µm polycarbonate membranes; Costar, Cambridge, Mass.) coated with amorphous collagen, 3) BIOCOAT Control Cell Culture Inserts (uncoated 1 µm PET membranes), and 4) uncoated Costar 0.45 µm polycarbonate membranes (TRANSWELL). Native fibrillar collagen cell culture substrates were prepared as in Example 1 and the cell culturing protocol used was as described in Examples 2 and 3, evaluating development of mannitol permeability coefficients with and without butyric acid induction.

Figure 2:
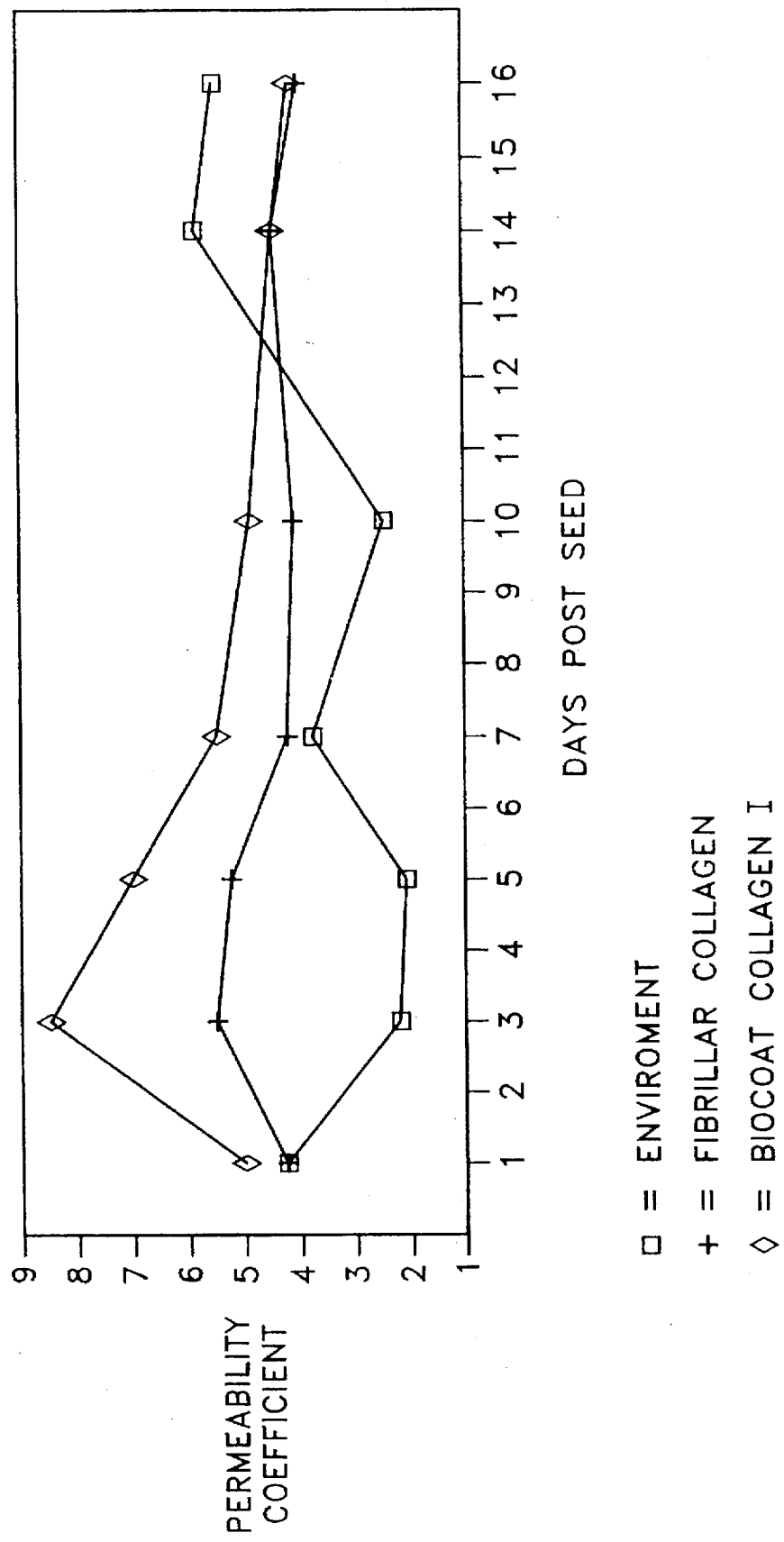
FIG. 2 is a graph showing the development of mannitol permeability coefficients in cells cultured on amorphous collagen (BIOCOAT Collagen I), native fibrillar collagen (Fibrillar Collagen) and native fibrillar collagen with butyric acid induction (Environment).
Figure 3:
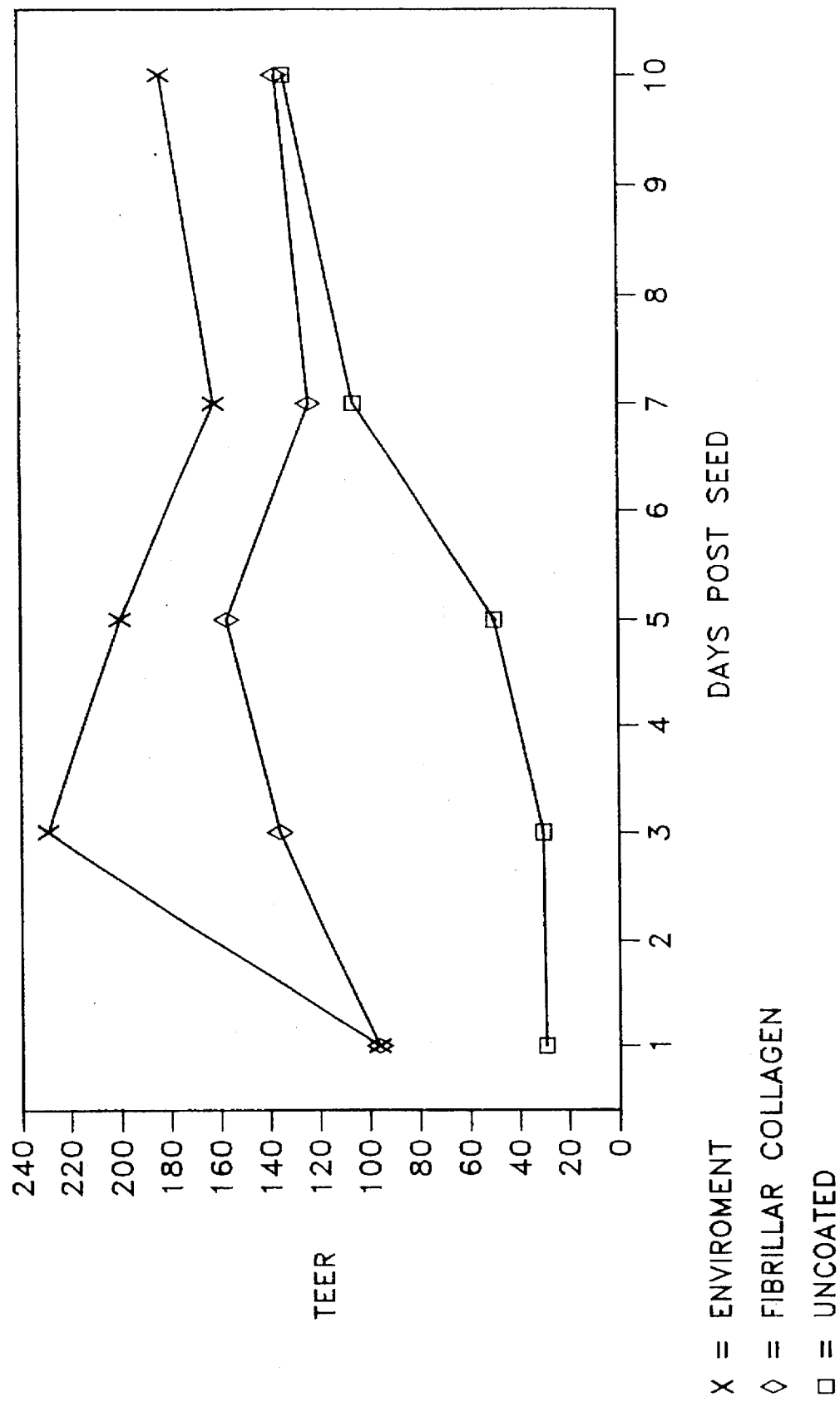
FIG. 3 is a graph showing the development of TEER in cells cultured on uncoated cell culture inserts (Uncoated), native fibrillar collagen (Fibrillar Collagen) and native fibrillar collagen with butyric acid induction (Environment).
Figure 4:
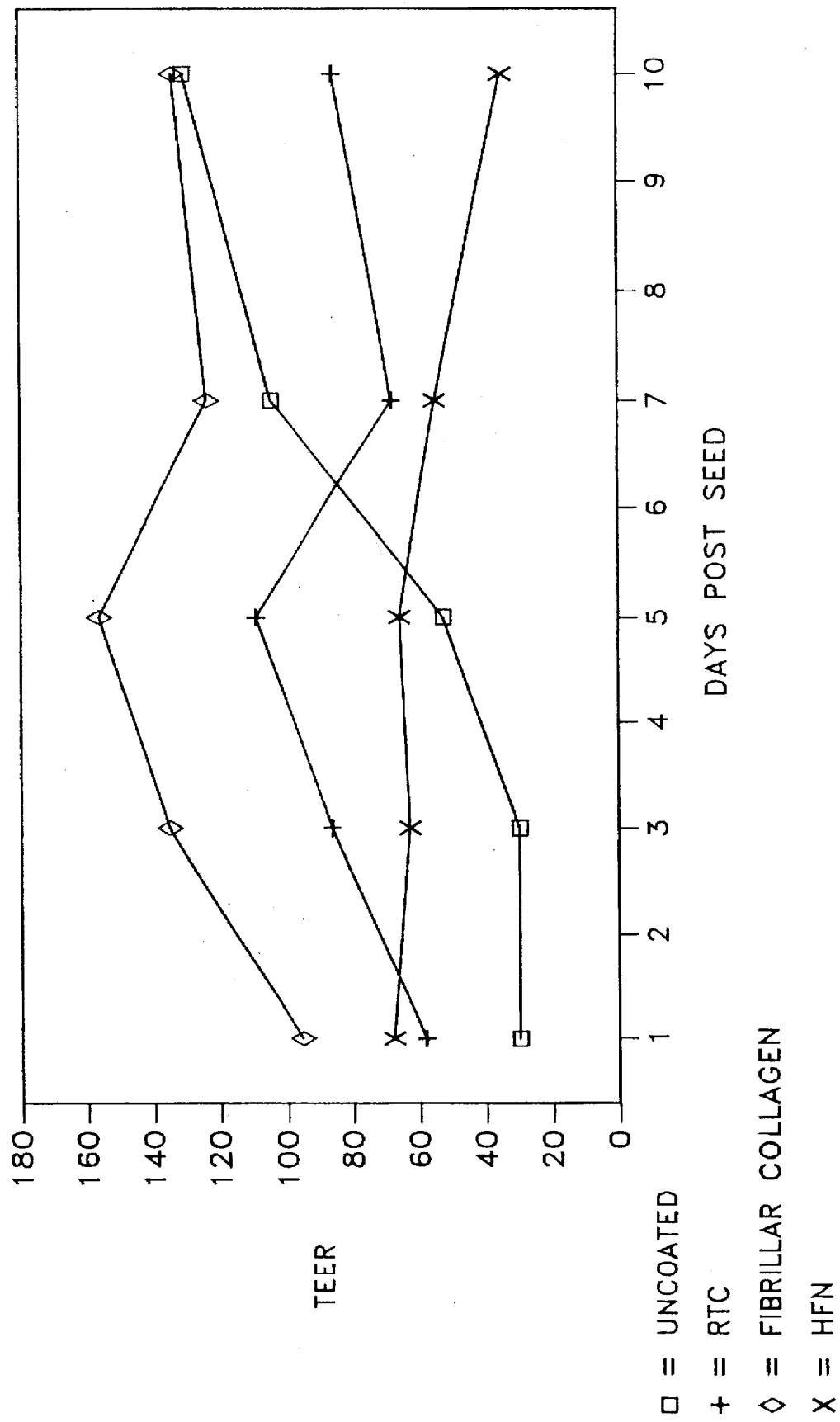
FIG. 4 is a graph showing the development of TEER in cells cultured on uncoated cell culture inserts (Uncoated), amorphous collagen (RTC), native fibrillar collagen (Fibrillar Collagen) and human fibronectin (HFN).

The results of the comparisons between commercial cell culture substrates and the native fibrillar collagen cell culture substrate are shown in FIGS. 2 and 3. Although neither the BIOCOAT Collagen I Cell Culture Insert or the native fibrillar collagen substrate alone induced development of permeability coefficients below 4×10⁻⁶ cmsec, cells cultured on the native fibrillar collagen cell culture substrates developed mannitol permeability coefficients of approximately 4×10⁻⁶ cmsec more rapidly than cells cultured on the BIOCOAT Collagen I Cell Culture Insert (approximately 7 days vs. approximately 14 days, FIG. 2). Induction with butyric acid (referred to herein as the "native fibrillar collagen/butyric acid environment") significantly enhanced the effect of the native fibrillar collagen cell culture insert on development of mannitol permeability coefficients, with the permeability coefficient falling to significantly less than 4×10⁻⁶ cmsec within 3 days after addition of butyric acid ("Environment," FIG. 2). Native fibrillar collagen cell culture substrates also promoted more rapid development of mature TEER values as compared to uncoated membranes (about 5 days vs.>10 days, FIG. 3), and the effect of the native fibrillar collagen was further enhanced by induction with butyric acid (within 3 days vs.>10 days, "Environment," FIG. 3). The native fibrillar collagen cell culture substrates similarly enhanced development of mature TEER values when compared to amorphous collagen substrates (about 5 days, FIG. 4). In this experiment, cell cultured on amorphous collagen substrates and uncoated membranes never reached TEER ≧150 ohmcm² (FIG. 4). Comparison of TEER with cells cultured on fibronectin substrates (HFN, FIG. 4) demonstrated that the differentiation-promoting effects of butyric acid are collagen-specific.

Figure 6:
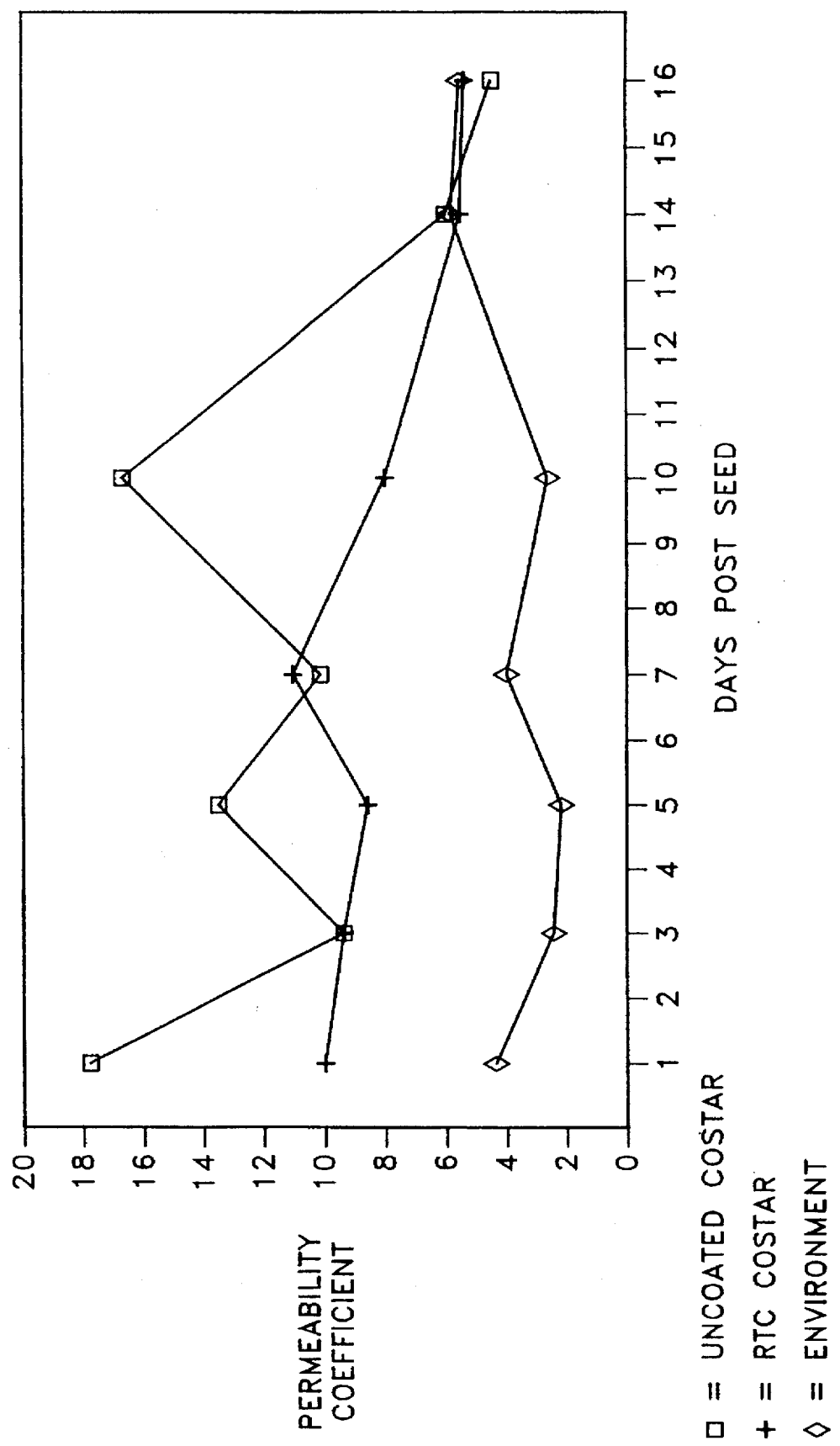
FIG. 6 is a graph showing the development of mannitol permeability coefficients in cells cultured on native fibrillar collagen with butyric acid induction according to the invention (Environment) as compared to prior art cell culture on amorphous collagen substrates (RTC Costar) and uncoated membranes (Uncoated Costar).

The Costar uncoated membrane, the Costar amorphous collagen-coated cell culture substrate (Costar) and the native fibrillar collagen cell culture substrate with butyric acid induction are compared in FIG. 6. Cells cultured on the amorphous collagen substrate exhibited less variability over the course of the experiment than did cells cultured on uncoated membranes, but still required 14-16 days to approach permeability coefficient values in the, $4 \times 10^{-6}$ cmsec range. Cells cultured in the native fibrillar collagen/butyric acid environment developed permeability coefficients below $4 \times 10^{-6}$ cmsec by 3 days and maintained these levels for over 10 days with little variability. It is believed that the initial permeability coefficient near $4 \times 10^{-6}$ cmsec seen in this experiment is due to the effect of the native fibrillar collagen cell culture substrate alone, as cells were cultured for 24 hrs. on the cell culture substrate prior to addition of butyric acid. FIG. 7 illustrates the effect of the native fibrillar collagen/butyric acid environment on cultured cells as compared to the two uncoated membranes. Again, the uncoated membranes were associated with significant variability in permeability coefficients over the course of the experiment. Variability in permeability coefficient was significantly reduced in cells cultured in the native fibrillar collagen/butyric acid environment, however. With the native fibrillar collagen/butyric acid environment, the permeability coefficient was initially close to $4 \times 10^{-6}$ cmsec, dropped below this value within 3 days, and was maintained at $\leq 4 \times 10^{-6}$ cmsec for the duration of the experiment. In contrast, cells cultured on the uncoated membranes did not develop permeability coefficients below $4 \times 10^{-6}$ cmsec and did not approach this value until about 14–16 days.

Figure 5:
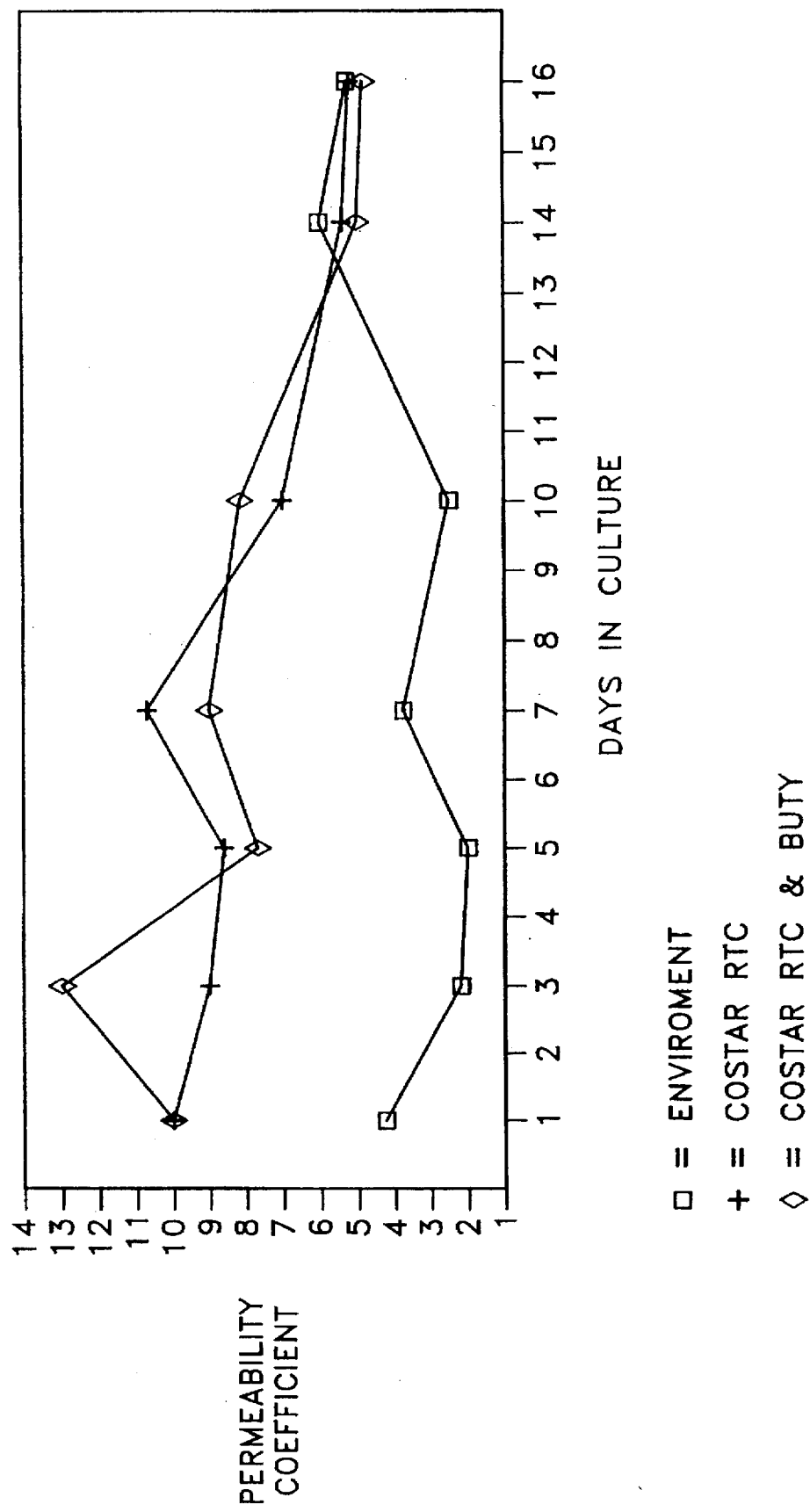
FIG. 5 is a graph showing the development of mannitol permeability coefficients in cells cultured on native fibrillar collagen with butyric acid induction (Environment), amorphous collagen coated on 0.45 µm polycarbonate membranes (Costar RTC) and amorphous collagen with butyric acid induction (Costar RTC & Buty.).

The synergistic enhancement of development of barrier function when butyric acid is added to cells cultured on the native fibrillar collagen cell culture substrates represents a specific interaction between the two components. FIG. 5 shows the comparison between development of permeability coefficients in cells cultured on amorphous collagen substrates alone ("Costar RTC"), cells cultured on amorphous collagen substrates with butyric acid induction ("Costar RTC & Buty.") and cells cultured in the native fibrillar collagen/butyric acid environment ("Environment"). Addition of butyric acid had little, if any, effect on the development of permeability coefficients when amorphous collagen was the cell culture substrate. Permeability coefficients were initially high and only gradually decreased over 16 days, never falling below $4 \times 10^{-6}$ cmsec. The native fibrillar collagen/butyric acid environment, however, induced initial permeability coefficients of about $4 \times 10^{-6}$ cmsec (1 day) which fell well below this value within 3 days. Permeability coefficients $\leq 4 \times 10^{-6}$ cmsec were maintained for between 10 and 14 days in the native fibrillar collagen/butyric acid environment.

In each of the experiments in which permeability coefficients in the native fibrillar collagen/butyric acid environment were evaluated, a slight increase in permeability coefficient was observed at about 14–16 days. Because the butyric acid remained in the culture throughout the experiment, this increase may be due to the effects on the cells of long term exposure to butyric acid, e.g., changes in the cell monolayer or the cell membrane which nonspecifically increase permeability. However, cells which are being cultured for permeability studies are used for the intended purpose soon after mature permeability coefficients have been reached, i.e., well before the observed increase in the permeability coefficient at 14–16 days.

What is claimed is:

1. A kit for promoting development of differentiated function in cultured epithelial cells comprising:

a) a cell culture medium for growth of epithelial cells;

b) a dried collagen film on a porous surface having an upper side and an underside, the dried collagen film produced by a process comprising the steps of
i) preparing solubilized collagen in liquid solution;
ii) polymerizing the collagen on the upper side of the porous surface in the presence of about 0.15–1.0M salt, to form a collagen gel;
iii) collapsing the collagen gel by removing entrapped liquid therefrom through the underside of the porous surface, and;
iv) drying the collapsed gel to form a film on the porous surface, and;

a differentiation inducing agent comprising about 4–20 mM butyric acid.

2. The kit of claim 1 wherein the dried collagen film is supported on a cell culture insert membrane.

3. The kit of claim 2 further comprising a serum-free media supplement.

4. The kit of claim 3 wherein the cell culture medium is DMEM and the differentiation inducing agent comprises about 5 mM butyric acid.

5. The kit of claim 3 further comprising a tissue culture dish.

* * * * *